| United States Patent [19] | [11] Patent Number: 4,931,578 |
| --- | --- |
| Ohta et al. | [45] Date of Patent: Jun. 5, 1990 |

[54] PROCESS FOR THE PRODUCTION OF TRIALKOXYSILANES

[76] Inventors: Yoshiro Ohta, 2113-12, Kamiiida-chou, Izumi-ku, Yokohama-shi, Kanagawa-ken; Mamoru Yoshizako, 131-21, Miwa-chou, Machida-shi, Tokyo, both of Japan

[21] Appl. No.: 158,480

[22] Filed: Feb. 22, 1988

[30] Foreign Application Priority Data

Feb. 23, 1987 [JP] Japan ................. 62-37895
May 21, 1987 [JP] Japan ................. 62-122455
Jun. 16, 1987 [JP] Japan ................. 62-147886

[51] Int. Cl.$^5$ ................................. C07F 7/18
[52] U.S. Cl. ................................. 556/470
[58] Field of Search ......................... 556/470

[56] References Cited

U.S. PATENT DOCUMENTS

| 2,445,576 | 7/1948 | Haber ................. 556/470 |
| --- | --- | --- |
| 2,650,204 | 8/1953 | Reynolds et al. ......... 556/470 X |
| 3,775,457 | 11/1973 | Muraoka et al. .......... 556/470 |
| 4,289,889 | 9/1981 | Herdle et al. ........... 556/470 |
| 4,727,173 | 2/1988 | Mendicino .............. 556/470 |
| 4,752,647 | 6/1988 | Inaba et al. ............ 556/470 |
| 4,762,939 | 8/1988 | Mendicino .............. 556/470 |
| 4,778,910 | 10/1988 | Stoffer et al. .......... 556/470 |

FOREIGN PATENT DOCUMENTS

| 55-72197 | 5/1980 | Japan ................. 556/470 |
| --- | --- | --- |
| 57-99593 | 6/1982 | Japan ................. 556/470 |
| 57-118592 | 7/1982 | Japan ................. 556/470 |
| 61-1694 | 1/1986 | Japan ................. 556/470 |
| 61-21478 | 5/1986 | Japan ................. 556/470 |

OTHER PUBLICATIONS

Inorg. Chem., vol. 9, No. 5, 1071–1975 (1970).

*Primary Examiner*—Paul F. Shaver
*Attorney, Agent, or Firm*—Armstrong, Nikaido, Marmelstein, Kubovcik & Murray

[57] ABSTRACT

This invention is concerned with an improved process for producing trialkoxysilanes comprising (i) an activation step where elemental silicon and a copper catalyst are activated, (ii) a reaction step where an alcohol is contacted with elemental silicon and the copper catalyst to allow it to react with the elemental silicon and (iii) a purification step where reaction product obtained is separated and/or refined, which is characterized in that a halide is introduced into the reaction system and/or mixture in one or more of the above steps (i) to (iii). With the introduction of a halide, the lowering in the selectivity of trialkoxysilanes can be prevented, and the percentage of elemental silicon reacted can be increased. In addition, the trialkoxysilanes contained in the reaction product can be stabilized.

12 Claims, No Drawings

PROCESS FOR THE PRODUCTION OF TRIALKOXYSILANES

BACKGROUND OF THE INVENTION

1. Field of the Invention

This invention relates to a process for producing trialkoxysilanes. In particular, it relates to a process for producing trialkoxysilanes in which elemental silicon is reacted with an alcohol in the presence of a copper catalyst to obtain the desired products in a high yield.

2. Description of the Prior Art

Trialkoxysilanes (e.g., trimethylsilane, triethylsilane, etc.) composed of a silicon atom bonded with three alkoxy groups and one hydrogen atom are highly unstable and reactive and, hence, undergo various reactions, such as addition, copolymerization, copolycondensation, disproportionation, etc., with other organic compounds, thereby yielding a variety of useful substances which can be utilized as raw materials for making silane coupling agents, coating agents, heat-resistant paints or silane gas to be used in the production of semiconductors.

Known processes for producing trialkoxysilanes include the one in which trichlorosilane is reacted with an alcohol in accordance with the following equation:

$$HSiCl_3 + 3ROH \rightarrow HSi(OR)_3 + 3HCl$$

(in which R represents an alkyl group) and the one in which elemental silicon is allowed to react with an alcohol in gas or liquid phase in the presence of a copper catalyst, whereby complicated reactions, including the following:

(1) $Si + 4ROH \rightarrow Si(OR)_4 + 2H_2$
(2) $Si + 3ROH \rightarrow HSi(OR)_3 + H_2$
(3) $Si + 2ROH \rightarrow H_2Si(OR)_2$
(4) $Si + 2ROH \rightarrow SiO_2 + 2RH$
(5) $ROH + H_2 \rightarrow RH + H_2O$
(6) Other products:

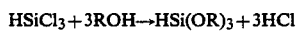

$H_2Si(OR)_2$, $RSi(OR)_3$, $(RO)_2Si-O-Si(OR)_2$,

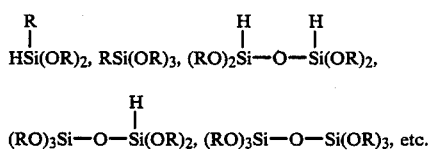

$(RO)_3Si-O-Si(OR)_2$, $(RO)_3Si-O-Si(OR)_3$, etc.

(in which R represents an alkyl group) take place, depending on reaction conditions (see, e.g., Inorg. Chem., Vol. 9, No. 5, 1071–1075 (1970)).

In the former process, desired trialkoxysilanes can be obtained only in a poor yield. The process also suffers from the problem that reactors used for the production are corroded by hydrogen halogenides produced as a by-product. It is thought that the corrosion occurs in accordance with the following mechanism: The by-product, i.e., hydrogen halogenides, react with alcohols to produce alkyl halides and water. The water so-produced hydrolyzes the raw material (trichlorosilane) and the products (tri- or tetra-alkoxysilanes), thereby forming polycondensation products.

In the latter process, alcohols are used in general in an excessive amounts in order to increase the reaction percentage (i.e., percentage reacted) and the reaction velocity of elemental silicon. In the case of a gas phase reaction, the reaction shown by the above formula (1) takes place predominantly, and reactions shown by the above formulas (4) (5) also take place because of high reaction temperature. Water formed in accordance with reaction formula (5) reacts with elemental silicon to form a film of silicic acid or silicon oxide (silica), or with the copper catalyst to form a copper oxide. Because of this, both of them become inactive and the reactions terminate midway, thus causing the problems that the reaction percentage of elemental silicon becomes lower and that the desired trialkoxysilanes can be obtained in a poor yield.

In cases where the latter process is carried out in a liquid phase, the reaction shown by formula (2) proceeds preferentially at the initial stage of the reaction and, hence, the desired trialkoxysilanes can be obtained with a good selectivity. However, with the progress of the reaction, the selectivity of trialkoxysilanes decreases gradually. It is therefore impossible to obtain the desired trialkoxysilanes in a satisfactorily high yield. The reason why the selectivity of trialkoxysilanes decreases with the progress of the reaction is not certain. It may however be explained as follows. Metallic elemental silicon used in industries usually contains various impurities, for example, alkali metals and/or alkaline earth metals, in an amount not greater than ca. 1% by weight. Such impurities react with alcohols to form metal alcolates which gradually accumulate with the progress of the reaction. With the increase in the quantity of accumulated metal alcolates, the pH value of the reaction system gradually shifts from acidic to neutral or basic. Because of this, once formed trialcoxysilanes are converted into tetraalkoxysilanes. With regard to the yield, it is considered to be important to activate elemental silicon and copper catalysts to the highest level possible and to suppress the above-described reactions (4) and (5) to the lowest level possible, by carrying out the reaction at a relatively low temperature.

The problems in the above liquid phase reaction can be solved by maintaining the acidity in the reaction system at a constant level, by using highly pure elemental silicon which is substantially free from the undesirable side reactions of alcohols with the impurities. However, purification of elemental silicon is highly time consuming and costly and, hence, it is virtually impossible to use highly pure elemental silicon which is pure enough not to cause the adverse effects in the production of trialkoxysilanes on a commercial scale.

The process in which elemental silicon is directly reacted with alcohols in gas or liquid phase in the presence of a copper catalyst also suffers from the problem that the reaction percentage of the alcohols is not high enough and, hence, the resulting reaction mixture contains large quantitis of unreacted alcohols, together with the desired trialkoxysilanes and other alkoxysilanes, such as tetraalkoxysilanes, dialkoxysilanes, dialkoxyalkylsilanes, trialkoxyalkylsilanes and dimers of these. In addition, the unreacted alcohols contained in the reaction mixture react with the desired trialkoxysilanes, thereby forming tetraalkoxysilanes, and the desired trialkoxysilanes undergo disproportionation to form dialkoxysilanes and tetralkoxysilanes in the course of purification or during storage before purification. As a result, the yield of trialkoxysilanes is markedly lowered.

Various methods have been proposed to solve the above problems. For example, the reaction product is stored at a temperature lower than 0° C., or a certain amino acid is added to the reaction mixture for its stabilization (see Japanese patent application (Laid Open) No. 72,197/80); an amine is added to the reaction mixture and its pH is adjusted to 2.0 to 7.0 (see Japanese Patent Application (Laid Open) No. 118,592/82; or trivalent organic phosphates (Japanese Patent Application (Publication) No. 21,478/86) or epoxides (Japanese Patent Application (Laid Open) No. 1,694/86) are added to the reaction mixture.

However, in cases where the temperature of the reaction mixture obtained is stored at 0° C. or below, refrigerators or freezers are required for its cooling. This makes its storage quite costly. In addition, the reaction mixture must be heated at the time when it is to be refined by means of rectification, which most likely results in decomposition of trialkoxysilanes. In cases where amino acids, amines, trivalent organic phosphates or epoxides are used as a stabilizer, refined trialkoxysilanes obtained by the distillation of the reaction mixture tend to be contaminated by the stabilizers used. In addition to this, those stabilizers did not always perform satisfactorily in preventing the reaction of trialkoxysilanes with unreacted alcohols. Or the disproportionation of trialkoxysilanes at the time of rectification of the reaction product, could not be sufficiently suppressed by the use of those stabilizers. In any case, the known stabilizers are by no means satisfactory.

In view of the above, the present inventors have conducted intensive investigations. As a result, it has now been found that, in the production of trialkoxysilanes comprising an activation step where elemental silicon and a copper catalyst are activated, a reaction step where an alcohol is contacted with elemental silicon and the copper catalyst so as to allow it to react with the elemental silicon and a purification step where the reaction mixture obtained is refined, the lowering in the selectivity of trialkoxysilanes can be prevented during the progress of the reaction, elemental silicon can be reacted at a high percentage and the trialkoxysilanes contained in the reaction mixture can be stabilized, by introducing a halogenide into, and allowing it to contact with, the reaction system and/or mixture in one or more of said steps.

SUMMARY OF THE INVENTION

It is therefore an object of the invention to provide a process for producing trialkoxysilanes wherein not only elemental silicon can be reacted at a high percentage but also the selectivity of trialkoxysilanes can be enhanced, and hence trialkoxysilanes can be produced at a high yield.

It is another object of the invention to provide a method for producing trialkoxysilanes wherein trialkoxysilanes contained in the reaction mixture can be stabilized and, hence, the reaction mixture can be easily rectified to give a highly pure trialkoxysilanes at a high yield.

It is a further object of the invention to provide a process for producing trialkoxysilanes wherein, in its activation step, metallic silicon and a copper catalyst are brought into contact with a halide in a gas or liquid phase, in order to increase the percentage of elemental silicon reacted and to improve the selectivity of trialkoxysilanes through the activation of the elemental silicon and the catalyst.

It is a still further object of the invention to provide a process for producing trialkoxysilanes wherein, in its reaction step where elemental silicon is reacted with an alcohol, a halide is introduced into the reaction system, so as to improve both the percentage of elemental silicon reacted and the selectivity of trialkoxysilanes.

It is a further object of the invention to provide a process for producing trialkoxysilanes wherein, in its purification step, a halide is added to the reaction mixture containing unreacted alcohols, so as to stabilize trialkoxysilanes contained therein.

Accordingly, there is provided by the invention a process comprising an activation step where elemental silicon and a copper catalyst are activated, a reaction step where an alcohol is contacted with elemental silicon and the copper catalyst so as to allow it to react with elemental silicon and a purification step where the reaction mixture obtained is purified, in which a halide is introduced into, and allowed to contact with, the reaction system and/or mixture in one or more of said steps.

In the present invention, a halide can be introduced and contacted in one of the production steps, including said activation, reaction and purification steps, or in all of the steps. It can be preferable to activate elemental silicon and a copper catalyst by allowing a halogenide to contact with them in a gas or liquid phase in the activation step. It can also be preferable to add a halogenide to the reaction system in said reaction step or to add it to the reaction mixture that contains unreacted alcohols in said purification step.

Elemental silicon to be used as a raw material in the process of the invention may have a purity of 80% by weight or above and may be in the form of granules having an average particle size not greater than 200 μm. It is possible to use, for example, commercially available low price products having a purity of from 80 to 99% by weight and an average particle size of 50 to 100 μm which may be produced by use of a vibrating mill, a ball mill, or the like. Usually, such a commercially available elemental silicon contains metals, such as Fe, Ca, Mg, Zn, Al, Ti, Cr, Ni, Mn, Ba, Cu and Zr, in an amount up to ca. 1% by weight, or at least in the order of parts per million.

Alcohols to be used as a raw material in the process of the invention include alkyl alcohols. It can be preferable to use alkyl alcohols having 1 to 6 carbon atoms, for example, methyl alcohol, ethyl alcohol, n-propyl alcohol, iso-propyl alcohol, n-butyl alcohol, iso-butyl alcohol, amyl alcohol and the like. These alcohols may have a purity of no less that 98% by weight, preferably 99.9% by weight or above and a water content not higher than 0.2% by weight, preferably not higher than 0.1% by weight. In ordinary cases, alcohols can be used in an amount of from 3 to 10 mol, per mol of elemental silicon. In order to improve the reaction percentage of elemental silicon (or percentage of metallic silicon reacted), it is preferable to use an excess of alcohol, preferably 4 to 8 mol, per mol of elemental silicon.

In the process of the invention, there can be used known copper catalysts, including, e.g., powders of elemental copper, and compounds of copper, such as cuprous chloride, cupric chloride, cuprous bromide, cupric bromide, cuprous iodide, cupric iodide, cupruos fluoride, copper formate, acetylacetonatocopper, cuprous acetate, cupric acetate, cuprous oxide, cupric oxide, and the like. These catalysts can be individually, or two or more of these can be used in combination. In usual cases, the copper catalysts are used in an amount of from 0.005 to 0.5 mol, preferably from 0.01 to 0.1 mol, per mol of elemental silicon. When the amount of copper catalysts is less than 0.005 mol, a lowering in the reaction percentage of elemental silicon will be resulted, whereas even if a copper catalyst is used in an amount exceeding 0.5 mol, no improvements will be attained in the reaction percentage of elemental silicon and in the selectivity of trialkoxysilanes, which is disadvantageous from economic view point. The copper catalysts may be premixed with elemental silicon and then subjected, prior to their use, to a heat treatment in nitrogen atmosphere at a temperature of from 200° to 600° C., preferably from 200° to 400° C., or in an appropriate solvent at a temperature of from 100° to 500° C., preferably from 200° to 400° C., for the purpose of their activation.

Halides to be used in the process of the invention may be either organic halogenides or inorganic halogenides. It can however be preferable to use organic halogenides. As examples of usable organic halogenides, mention may be made of alkyl halogenides, such as methyl chloride, methyl bromide, methyl fluoride, methyl iodide, ethyl chloride, ethyl bromide, ethylfluoride, ethyl iodide, n-propyl chloride and n-propyl bromide; alkenyl halogenides, such as dichloromethane and dichloroethane; aryl halogenides, such as chlorobenzene and dichlorbenzene; and other organic acid halides, such as chloroform, carbon tetrachloride, acetyl chloride, and the like. As examples of usable inorganic halides, mention may be made of hydrogen halogenides, such as hydrogen chloride, hydrogen bromide, hydrogen fluoride and hydrogen iodide; ammonium halogenides, such as ammonium chloride, ammonium bromide, ammonium fluoride and ammonium iodide; and other organic compounds, such as trimethylamine hydrochloride, trimethylamine hydrobromide, triethylamine hydrochloride, triethylamine hydrobromide, tetramethylammonium chloride, tetramethylammonium bromide, choline chloride and choline bromide.

The amount of halides to be used varies, depending on the step where it is to be introduced. In the case where elemental silicon and a copper catalyst are subjected to activation in a gas or liquid phase, by allowing them to contact with a halide, the halogenide is used in usual cases in an amount of from 0.0001 to 1 mol, preferably from 0.001 to 0.5 mol, per mol of metallic silicon. When the amount is less than 0.0001 mol, the elemental silicon and copper catalyst will not be activated sufficiently. In addition to this, alcolates of alkali and alkaline earth metals, which are contained as impurities in elemental silicon, will be formed in greater amounts, thus making the reaction system basic and, hence, causing a lowering in the selectivity of trialkoxysilanes. On the other hand, when the amount of halogenide used is greater than 1 mol, the reaction system becomes excessively acidic, and a lowered selectivity of trialkoxysilanes will be resulted. It is also disadvantageous from economic view point. In the case where a halogenide is introduced in the reaction step, the halogenide is used usually in an amount of from 0.0001 to 1 mol, preferably from 0.001 to 0.5 mol, per mol of alcohol. When the amount is less than 0.0001 mol, alcolates of alkali or alkaline earth metals, which are contained as impurities in metallic silicon, are formed, thus making the reaction system neutral or basic and, hence, causing a lowering in the amount of trialkoxysilanes formed. On the other hand, when the amount is greater than 1 mol, the reaction system becomes excessively acidic, and a lowered selectivity of trialkoxysilanes will be resulted. It is also disadvantageous from economic view point. In cases where a halogenide is introduced in the activation or reaction step, it can be employed in a pure form. It can however be advantageous, with regard to convenience in handling and in the control of volume, to introduce a halogenide in the form of a mixture with an inactive gas (e.g., nitrogen gas) or hydrogen gas. In the case where a halogenide is added to the reaction mixture containing unreacted alcohols, the halogenide is used usually in an amount of from 0.0001 to 20% by weight, preferably from 0.001 to 10% by weight, more preferably from 0.01 to 6% by weight, based on the weight of the reaction mixture obtained. When the amount of halogenide used is less than 0.0001%, it will not be possible to attain a sufficient stabilization effect, whereas when it is used in an amount greater than 20% by weight, no additional stabilizing effect will be attained. It is disadvantageous from economic view point.

In the case where the process of the invention is carried out in a liquid phase, any solvent can be used if it is stable in the reaction system and can be heated to the required reaction temperature. As examples of usable solvents, mention may be made of various hydrocarbons, including paraffinic hydrocarbons, such as octane, decane, dodecane, tetradecane, hexadecane, octadecane, eicosane, etc.; hydrocarbons of alkylbenzene series, such as ethylbenzene, trimethylbenzene, cymene, diethylbenzene, butylbenzene, butyltoluene, octylbenzene, dodecylbenzene, didodecylbenzene, etc., and hydrogenated derivatives thereof; hydrocarbons of diphenyl series, such as diphenyl, diphenyl ether, monoethyldiphenyl, diethyldiphenyl, triethyldiphenyl, etc., and hydrogenated derivatives thereof; hydrocarbons of alkylnaphthalene series and hydrogenated derivatives thereof; hydrocarbons of triphenyl series and hydrogenated derivatives thereof; and the like. It is possible to use one single solvent or to use more than one solvent in combination. Of these solvents, those which do not generate foams in the course of the reaction and have a boiling point of from 100° to 500° C., preferably from 200° to 400° C., at ordinary pressure can be preferable. Although it is possible to use different solvents for the activation step and for the reaction step, it is preferable to use the same solvent for both of the steps since it can be advantageous to carry out those two steps continuously.

In cases where a hydrogenide is allowed to contact with elemental silicon and a copper catalyst in a liquid phase, so as to effect their activation, the process of the invention can be carried out, for example, in the following manner.

Into a reactor equipped with a stirrer, an alcohol introduction tube, a halide introduction tube, a product flow-out tube and a thermometer are charged elemental silicon, a copper catalyst and a reaction solvent. While an inactive gas (e.g., nitrogen) or hydrogen gas is being blown, if necessary, into the reactor, a halide or a mixture of a halide and an inactive gas or hydrogen gas is introduced thereinto with stirring at the boiling point of the solvent (usually which is in the range of from 100° to 500° C.), preferably at a temperature of from 200° to 400° C., whereby the elemental silicon and the copper catalyst are allowed to contact with the halide for a certain period of time, for the purpose of their activation. If desired, the heating is continued under an atmosphere of an inactive gas or hydrogen gas for their ripening.

After the completion of the activation treatment, an alcohol is introduced into the reactor at a constant rate through the alcohol introduction tube, so as to allow it to react with the elemental silicon, and the reaction products that flow out of the product flow-out tube are cooled by a condenser connected to the outlet thereof, to collect the desired trialkoxysilanes and unreacted alcohols. It can be preferable to use, in this step, an alcohol containing a small quantity of halide or to introduce, through the halide introduction tube, a small quantity of halide, which may or may not be diluted with an inactive gas of hydrogen gas, so as to maintain the pH of the reaction system and the desired trialkoxysilanes flowing out of the reactor in the range of from 1 to 6, preferably from 2 to 4. This makes it possible to further improve the selectivity of trialkoxysilanes.

In cases where elemental silcon and a copper catalyst are allowed to contact with a halogenide in a gas phase in order to effect the activation thereof, there can be used known vertical-type or horizontal-type reactors in accordance with conventional methods. In this case, the activation treatment can be effected by introducing a halogenide, which may or may not be diluted with an inactive gas or hydrogen gas, into a reactor charged with elemental silicon and a copper catalyst and heated to a temperature of from 150° to 600° C., preferably from 200° to 400° C. It can be preferable to continue the heating with continued introduction of an inactive gas or hydrogen gas for a predetermined period of time, so as to ripen the contents of the reactor.

When the elemental silicon is consumed by the reaction with an alcohol following the activation step, it is possible to charge into the reactor an additional amount of elemental silicon (and an additional amount of copper catalyst may also be charged thereinto although it is not required in ordinary cases), and the same activation and reaction steps can be repeated, so as to repeatedly produce desired trialkoxysilanes in the same reactor.

In cases were a halide is added to the reaction system, the process of the invention can be carried out, for example, in the following manner.

Into a reactor equipped with a stirrer, an alcohol introduction tube, an organic halide introduction tube, a product flow-out tube and a thermometer are charged powders of elemental silicon, a solvent and a copper catalyst. If desired, the powders of the elemental silicon and the copper catalyst can be ripened by allowing them to contact each other with stirring under nitrogen atmosphere for a predetermined period of time at a temperature of from 100° to 300° C. Thereafter, an alcohol and an organic halide are introduced into the reactor through the alcohol introduction tube and the halogenide introduction tube, respectively, at a constant rate, and the reaction products that flow out of the product flow-out tube are cooled by a condenser connected to the outlet thereof, so as to collect the desired trialkoxysilanes and unreacted alcohols.

In cases where a halide is added in the purification step to the resulting reaction mixture containing unreacted alcohols, the process of the invention can be carried out, for example, in the following manner.

After the completion of the reaction of elemental silicon with an alcohol which is carried out in the presence of a copper catalyst, a certain amount of halide is added to the resulting reaction mixture, and desired trialkoxysilanes are purified by distilling the reaction mixture in the presence of the halide. The halide can be added to the reaction mixture either immediately after the completion of the reaction of the metallic silicon with the alcohol, or just before the distillation of the reaction mixture. It can however be preferable to add it into the reaction mixture immediately after the completion of the reaction.

It is presumed that reactions set forth below take place in the system when elemental silicon and a copper catalyst are subjected to activation through contact with a halide.

$$CuCl + Si \rightarrow SiCl_4 + Cu$$

$$2Cu + RCl \rightarrow CuCl + RCu$$

$$3(Si + 2RCl) \rightarrow R_2SiCl_2 + RSiCl_3 + R_3SiCl$$

Because of the above reaction, elemental silicon and copper catalysts can be activated, and their reactivity with alcohols can be enhanced. In addition, undesirable side reactions can be suppressed and, hence, the reaction percentage of elemental silicon and the selectivity of trialkoxysilanes can be improved.

Moreover, alcolates which may be generated by the reaction of alcohols with alkali metals and/or alkaline earth metals, which are contained in elemental silicon as impurities, can be neutralized by halide or by the combination of elemental silicon, copper catalyst and halide. Accordingly, the reaction system can always be maintained in an acidic state. This prevents once formed trialkoxysilanes to be converted into tetra-alkoxysilanes and contributes to maintain the selectivity of trialkoxysilanes to a high level. In addition, the stability of the reaction products can also be improved, although the reason for the stabilization effect has not been theoretically elucidated.

Taking the above into consideration, it is assumed that reactions as set forth below take place in the system.

(1) $Si + 2RCl \rightarrow RSiCl_3 + R_2SiCl_2 + R_3SiCl$
(in which R is an alkyl group, such as methyl, ethyl, etc.)

(2) $(RSiCl_3 + R_2SiCl_2 + R_3SiCl) + ROH \rightarrow R_xSi(OR)_yCl_z + yHCl$
(in which x, y and z are 1, 2 or 3)

(3) $RCl + MOR \rightarrow MCl + ROH$
(in which M is a metal, such as Ca, Al, Zn, Mg, Na, K, Ni, Ba, etc.)

(4) $2Cu + RCl - CuCl + RCu$

DETAILED DESCRIPTION OF PREFERRED EMBODIMENTS

The invention will further be explained by way of examples and comparative examples.

EXAMPLE 1

Into a 500 ml reactor equipped with a stirrer, an alcohol introduction tube, a halide introduction tube, a product flow-out tube and a thermometer were charged 150 g of elemental silicon having a purity of 98 wt % and an average particle size of ca. 50 μm [impurities: Fe, 0.83 wt %; Ca, 0.35 wt %; Mg, 150 ppm; Zn, 320 ppm; Al, 0.60 wt %; Ti, 860 ppm; Cr, 40 ppm; Ni, 43 ppm; Mn, 240 ppm; Ba, 50 ppm; Cu, 32 ppm; and Zr, 180 ppm (determined by ICP emission spectral analysis], 300 ml of hydrocarbons of alkylbenzene series having boiling points of from 280° to 300° C. (AB-HL marketed by Mitsubishi Petrochemical Co., Ltd.) and 7.5 g of cuprous chloride. A condenser was attached to the outlet of the flow-out tube.

While being stirred, the contents of the reactor were heated up to 200° C. over a period of 60 minutes, during which nitrogen gas was introduced into the reactor at a rate of 30 ml/min. Subsequently, 20 ml/min of nitrogen gas and 10 ml/min of gaseous methyl chloride were introduced thereinto at a temperature of from 200° to 260° C. for a period of 10 hours, and then the introduction of methyl chloride was stopped and the contents were ripened at a temperature of 200° to 230° C. for a period of 4 hours, with continued introduction of nitrogen gas at a rate of 20 ml/min.

After the activation of the elemental silicon and the cuprous chloride, liquid methyl alcohol of 99.9 wt % purity or above was introduced into the reactor through the alcohol introduction tube at a rate of 25 g/hr and, at the same time, 2 ml/min of gaseous methyl chloride and 10 ml/min of nitrogen gas were introduced thereinto through the halogenide introduction tube, during which the reaction temperature was maintained at 160° to 170° C. This reaction was continued for 40 hours, and the reaction product flowing out of the product flow-out tube was cooled by the condenser connected to its outlet. There was obtained 980 g of reaction product.

The thus obtained reaction product contained 46.4 wt % of desired trimethoxysilane, 9.5 wt % of tetramethoxysilane, 39.1 wt % of unreacted methyl alcohol, 0.2 wt % of dimethoxysilane, 0.6 wt % of methyldimethoxysilane, 1.1 wt % of methyltrimethoxysilane, a total of 1.1 wt % of three different kinds of dimers, and 3.0 wt % of the solvent (determined by gas cromatography). The reaction percentage of the elemental silicon (i.e., percentage of elemental silicon reacted) was 81.0% by weight, and the selectivity of trimethoxysilane was 88.2% by mol.

The reaction product was charged into a container and tightly sealed. After being allowed to stand for 15 days at 20° C., it was again analyzed by gas chromatograpy. There was observed no change in its composition. This proves that the reaction product is highly stable.

EXAMPLE 1

Example 1 was repeated, except that elemental silicon and cuprous chloride were not subjected to the activation treatment using methyl chloride. There was obtained 970 g of reaction product.

The thus obtained reaction product contained 25.1 wt % of desired trimethoxysilane, 24.2 wt % of tetramethoxysilane, 46.1 wt % of unreacted alcohol, and 4.6 wt % of other compounds. The reaction percentage of the elemental silicon was 66.3% by weight, and the selectivity of trimethoxysilane was 56.7% by mol.

EXAMPLE 2

Into a Pyrex glass tube of 30 mm diameter were charged 150 g of elemental silicon and 7.5 g of cuprous chloride, both the elemental silicon and the cuprous chloride used being the same as those used in Example 1. It was heated by a band heater up to 250° C. over 2 hours, during which nitrogen gas was passed therethrough at a rate of 20 ml/min. Subsequently, 20 ml/min of nitrogen gas and 10 ml/min of gaseous methyl chloride were introduced thereinto at a temperature of from 250° to 300° C. for a period of 4 hours. Then, the heating and the introduction of gaseous methyl chloride were stopped, and the contents were ripened for 3 hours with introduction of 20 ml/min of nitrogen gas, during which the temperature of the contents was dropped to 50° C.

The thus obtained elemental silicon and cuprous chloride were placed in a reactor, and methyl alcohol was introduced under the same conditions as in Example 1. There was obtained 990 g of reaction product.

The thus obtained reaction product contained 44.5 wt % of desired trimethoxysilane, 10.3 wt % of tetramethoxysilane, 37.6 wt % of unreacted methyl alcohol, and 2.2 wt % of other compounds (determined by gas chromatography). The reaction percentage of the metallic silicon was 80.4% by weight, and the selectivity of trimethoxysilane was 84.3% by mol.

EXAMPLE 3

Into an 8 liter stainless steel reactor similar to the one used in Example 1 were charged 2 kg of elemental silicon, 100 g of cuprous chloride and 4 liters of hydrocarbons of alkylbenzene series, the three components used being the same as those used in Example 1. While being stirred, 20 ml/min of nitrogen gas and 10 ml/min of gaseous methyl chloride were introduced into the reactor at a temperature of 200° to 260° C. for a period of 6 hours, and then 30 ml/min of nitrogen gas and 10 ml/min of gaseous methyl chloride were introduced thereinto at a temperature of 200° to 230° C. for a period of 6 hours. The heating and the introduction of methyl chloride were stopped, and the contents were ripened for 2 hours with continued introduction of 30 ml/min of nitrogen gas, during which the temperature of the contents was dropped to 160° C.

After activation of the elemental silicon and the cuprous chloride, liquid methyl alcohol was introduced into the reactor at a rate of 145 g/hr and, at the same time, 3 ml/min of gaseous methyl chloride and 20 ml/min of nitrogen gas were introduced thereinto through the halogenide introduction tube, during which the reaction temperature was maintained at 160° to 170° C. This reaction was allowed to continue for 40 hours to obtain 5,750 g of product for the first reaction.

The thus obtained product contained 71.0 wt % of trimethoxysilane, 18.5 wt % of tetramethoxysilane, 5.1 wt % of unreacted methyl alcohol, and 4.5 wt % of other compounds (determined by gas chromatography).

The reaction percentage of the elemental silicon was 56.7% by weight, and the selectivity of trimethoxysilane was 82.7% by mol.

Subsequently, liquid methyl alcohol was introduced into the reactor at a rate of 94 g/hr for a period of 30 hours under the same conditions as above, to obtain 2,680 g of product for the second reaction.

The thus obtained product contained 51.2 wt % of desired trimethyoxysilane, 33.5 wt % of tetramethoxysilane, 9.8 wt % of unreacted methyl alcohol, and 6.5 wt % of other compounds (determined by gas chromatography). The overall reaction percentage of the elemental silicon for the first and second reaction was 80.7 % by weight, and the overall selectivity of trimethoxysilane was 65.5% by mol.

After the completion of the second reaction, 1.5 Kg of elemental silicon was charged into the reactor (no additional copper catalyst was charged), and the contents were subjected to the same activation treatment as above. Thereafter, liquid methyl alcohol was introduced thereinto at a rate of 140 g/hr and, at the same time, gaseous methyl chloride and nitrogen gas were introduced at a rate of 3 ml/min and 20 ml/min, respectively, during which the reaction temperature was maintained at 160° to 180° C. This reaction was continued for 30 hours to obtain 4,100 g of reaction product for the third reaction. The thus obtained product contained 68.0 wt % of desired trimethoxysilane, 21.0 wt % of tetramethoxysilane, 7.8 wt % of unreacted methyl alcohol, and 3.2 wt % of other compounds (determined by gas chromatography). The reaction percentage of the elemental silicon was 53.2% by weight (based on the quantity of the additional metallic silicon), and the selectivy of trimethoxysilane was 80.1% by mol.

Subsequently, liquid methyl alcohol was introduced into the reactor at a rate of 90 g/hr for a period of 25 hours under the same conditions as above, to obtain 2,140 g of product for the fourth reaction. The thus obtained reaction product contained 50.0 wt % of trimethoxysilane, 31.0 wt % of tetramethoxysilane, 11.6 wt % of unreacted methyl alcohol, and 7.4 wt % of other compounds. The overall reaction percentage of the elemental silicon for the third and fourth reactions was 78.4% by weight (based on the quantity of the additional elemental silicon), and the overall selectivity of trimethoxysilane was 67.3% by mol.

EXAMPLE 3

The first and second reactions of Example 3 were repeated under the same conditions, except that methyl chloride was not introduced in the activation treatment of elemental silicon and cuprous chloride and the reaction temperature was maintained at 200° C. There were obtained 5,680 g of product in the first reaction and 2,590 g of product in the second reaction.

The product of the first reaction contained 29.0 wt % of desired trimethoxysilane, 33.4 wt % of tetramethoxysilane, 32.5 wt % of unreacted methyl alcohol, and 5.1 wt % of other compounds, and the product of the second reaction contained 21.2 wt % of desired trimethoxysilane, 31.4 wt % of tetramethoxysilane, 39.4 wt % of unreacted methyl alcohol, and 8.0 wt % of other compounds. The overall reaction percentage of the elemental silicon for the first and second reactions was 50.2% by weight, and the selectivity of trimethoxysilane was 46.4% by mol.

EXAMPLE 4

Example 1 was repeated, except that ethyl alcohol was used in place of methyl alcohol and ethyl chloride was used in place of methyl chloride, said ethyl alcohol being supplied at a rate of 25 g/min and the temperature of the reaction being maintained at 200° to 220° C. There was obtained 940 g of reaction product. The thus obtained product contained 43.2 wt % of desired triethoxysilane, 15.4 wt % of tetraethoxysilane, 35.3 wt % of unreacted ethyl alcohol, and 6.1 wt % of other compounds (determined by gas chromatography). The reaction percentage of the elemental silicon was 60.2% by weight, and the selectivity of triethoxysilane was 78.4% by mol.

EXAMPLE 4A

Example 4 was repeated, except that ethyl chloride was not introduced in the activation step. There was obtained 930 g of reaction product. The thus obtained product contained 17.1 wt % of triethoxysilane, 21.0 wt % of tetraethoxysilane, 54.8 wt % of unreacted ethyl alcohol, and 7.1 wt % of other compounds (determined by gas chromatography). The reaction percentage of the elemental silicon was 35.0% by weight, and the selectivity of triethoxysilane was 50.3% by mol.

EXAMPLE 5

Example 1 was repeated, except that hydrogen chloride was used in place of methyl chloride for the activation of elemental silicon and cuprous chloride. There was obtained 955 g of reaction product. The thus obtained product contained 45.5 wt % of desired trimethoxysilane, 10.6 wt % of tetramethoxysilane, 38.5 wt % of unreacted methyl alcohol, and 5.4 wt % of other compounds (determined by gas chromatography). The reaction percentage of the elemental silicon was 78.9% by weight, and the selectivity of trimethoxysilane was 84.2% by mol.

EXAMPLE 6

Into a 500 ml reactor equipped with a stirrer, an alcohol introduction tube, an organic halogenide introduction tube, a product flow-out tube and a thermometer were charged 150 g of elemental silicon having an average particle size of ca. 50 μm, 300 ml of hydrocarbons of alkylbenzene series and 7.5 g of cuprous chloride, as in Example 1. A condenser was attached to the outlet of the product flow-out tube.

While being stirred, the contents of the reactor was heated to 200° to 250° C. and the elemental silicon was allowed to contact with the cuprous chloride for a period of 5 hours, during which nitrogen gas was introduced at a rate of 100 ml/min. Thereafter, liquid methyl alcohol of 99.9 wt % purity or above was introduced into the reactor at a rate of 30 ml/hr through the alcohol introduction tube, and gaseous methyl chloride at a rate of 20 ml/min through the halogenide introduction tube, thereby maintaining the reaction temperature at 180° C. This reaction was continued for 40 hours, and the reaction product flowing out of the product flow-out tube was cooled by the condenser connected to its outlet. There was obtained 1,040 g of reaction product.

The composition of the thus obtained product was analyzed by gas chromatography. It contained 44.33 wt % of desired trimethoxysilane 8.75 wt % of tetramethoxysilane, and 46.92 wt % of unreacted methyl alcohol. The reaction percentage of the elemental silicon was 81% by weight, and the selectivity of trimethoxysilane was 86% by mol.

The reaction product was charged into a container and tightly sealed. After being allowed to stand for 4 days at 18° C., it was again analyzed by gas chromatography. There was observed no change in its composition. This proves that the reaction product is highly stable.

EXAMPLE 7

In a porcelain mill, 500 g of powders of metallic silicon and 25 g of cuprous chloride were pulverized and admixed for 8 hours, both the elemental silicon and the cuprous chloride being the same as those used in Example 6. The resulting mixture was charged into a silica tube and heated at 600° C. for 3 hours under nitrogen atmosphere, thereby using an electric furnance.

Into a stainless steel reactor having a diameter of 10 cm and a height of 23 cm and equipped with a stirrer, an alcohol introduction tube, an organic halide introduction tube, a product flow-out tube and a thermometer were charged the mixture of the elemental silicon and the cuprous chloride prepared above, and 900 ml of hydrocarbons of alkyl benzene series having a boiling point of 280°~300° C., the same solvent as the one used in Example 6. Liquid methyl alcohol of 99.9 wt % purity or above was introduced into the reactor at a rate of 30 ml/hr and, at the same time, gaseous methyl chloride was introduced thereinto at a rate of 30 ml/min, during which the reaction temperature was maintained at 180° C. as in Example 6. This reaction was continued for 100 hours, and the product flowing out of the product flow-out tube was cooled by a condenser connected to its outlet. There was obtained 2,350 g of reaction product.

The composition of the thus obtained reaction product was analyzed as in Example 6. It contained 57.45 wt % of desired trimethoxysilane, 12.38 wt % of tetramethoxysilane, and 30.17 wt % of unreacted methyl alcohol. The reaction percentage of the metallic silicon was 72% by weight, and the selectivity of trimethoxysilane was 85% by mol. After being allowed to stand in a tightly sealed container at 16° C. for 5 days, the product was again analyzed by gas chromatography. There was observed no change in its composition. This proves that the reaction product is highly stable.

COMPARATIVE EXAMPLE 4

Example 6 was repeated, except that methyl chloride was not introduced at all. There was obtained 1,050 g of reaction product.

The composition of the thus obtained reaction product was analyzed as in Example 6. It contained 11.52 wt % of desired trimethoxysilane, 23.33 wt % of tetramethoxysilane, and 65.15 wt % of unreacted methyl alcohol. The reaction percentage of the elemental silicon was 49% by weight, and selectivity of trimethoxysilane was 38% by mol. After being allowed to stand in a tightly sealed container at 18° C. for 4 days, the composition of the reaction product was again analyzed by gas chromatography. The content of desired trimethoxysilane decreased to 5.06% by weight, and the content of tetramethoxysilane increased to 29.81% by weight.

COMPARATIVE EXAMPLE 5

Example 7 was repeated, except that methyl chloride was not introduced at all. There was obtained 2,460 g of reaction product.

The composition of the thus obtained reaction product was analyzed as in Example 6. It contained 16.87 wt % of desired trimethoxysilane, 39.84 wt % of tetramethoxysilane, and 43.29 wt % of unreacted methyl alcohol. The reaction percentage of the elemental silicon was 55% by weight, and the selectivity of trimethoxysilane was 35% by mol. After being allowed to stand in a tightly sealed container at 16° C. for 5 days, the composition of the reaction product was again analyzed by gas chromatography. The content of desired trimethoxysilane decreased to 8.33% by weight, and the content of tetramethoxysilane increased to 48.34% by weight.

EXAMPLE 8

In a porcelain mill, 100 g of powders of elemental silicon and 5 g of cuprous chloride were pulverized and admixed for 8 hours, both the elemental silicon and cuprous chloride being the same as those used in Example 6. The resulting mixture was charged into a silica tube and heated at 600° C. for 3 hours under nitrogen atmosphere, thereby using an electric furnance.

Into a 500 ml reactor equipped with a stirrer, an alcohol introduction tube, an organic halogenide introduction tube, a product flow-out tube and a thermometer were charged the mixture of the elemental silicon and the cuprous chloride prepared above, and 300 ml of hydrocarbons of alkylbenzene series having a boiling point of from 280° to 300° C., the same solvent as the one used in Example 6. A liquid ethyl alcohol containing 2.5% by weight of ethyl chloride was introduced into the reactor at a rate of 30 ml/hr, during which the temperature inside of the reactor was maintained at 200° C. This reaction was continued for 20 hours, and the product flowing out of the product flow-out tube was cooled by a condenser connected to its outlet. There was obtained 400 g of reaction product.

The composition of the reaction product obtained was analyzed as in Example 6. It contained 35 wt % of desired triethoxysilane, 11 wt % of tetraethoxysilane, and 40 wt % of unreacted alcohol. The reaction percentage of the elemental silicon was 30% by weight, and the selectivity of triethoxysilane was 80% by mol.

COMPARATIVE EXAMPLE 6

Example 8 was repeated, except that ethyl chloride was not introduced at all. There was obtained 420 g of reaction product.

The composition of the thus obtained reaction product was analyzed as in Example 8. It contained 7 wt % of desired triethoxysilane, 24 wt % of tetraethoxysilane, and 71 wt % of unreacted ethyl alcohol. The reaction percentage of the elemental silicon was 18% by weight, and the selectivity of triethoxysilane was 26% by mol.

EXAMPLE 9

In a porcelain mill, 500 g of elemental silicon having an average particle size of 200 μm and 25 g of cuprous chloride were pulverized and admixed for 2 hours. The resulting mixture was charged into a silica tube and heated at 600° C. for 3 hours under nitrogen atmosphere, thereby using an electric furnance.

Into a stainless steel reactor having a diameter of 10 cm and a height of 23 cm and equipped with a stirrer, an alcohol introduction tube, a nitrogen introduction tube, a product flow-out tube and a thermometer were charged the mixture of elemental silicon and the cuprous chloride prepared above, and 1,000 liters of the same hydrocarbons of alkylbenzene series as the one used in Example 1. The reaction was allowed to proceed for 80 hours at a temperature of from 170° to 180° C., during which 30 ml/hr of methyl alcohol having a purity of 99.9 wt % or above and 20 ml/min of nitrogen gas were introduced into the reactor, and 2,280 g of reaction mixture was recovered through the product flow-out tube. The reaction mixture contained 13.3 wt % of methanol, 60.8 wt % of trimethoxysilane, 21.5 wt % of tetramethoxysilane, and 4.4 wt % of other compounds (determined by gas chromatography). The reaction percentage of the elemental silicon was 81.9% by weight, and the selectivity of trimethoxysilane was 77.9% by mol.

The thus obtained reaction mixture was divided into two portions. To one portion (Mixture A) was added 23 g (ca. 2% by weight) of methyl chloride, whereas nothing was added to the other portion (Mixture B). The Mixtures A and B were separately fractionated, by means of distillation, into initial fraction (which had a boiling point up to 60° C.), main fraction (which had a boiling point of from 79° to 81° C.), post fraction (which had a boiling point of from 120° to 122° C.), and residue. Each of them were analyzed by gas chromatograpy. Results of the fractionation are shown in Table 1, and the results of the chromatographic analysis are shown in Table 2.

TABLE 1

| Mixture | Initial Fraction | Main Fraction | Post Fraction | Residue |
|---|---|---|---|---|
| A | 319 g | 523 g | 239 g | 59 g |
| B | 239 g | 425 g | 417 g | 59 g |

TABLE 2

| Composition (Wt %) | Mixture A | | | | Mixture B | | | |
|---|---|---|---|---|---|---|---|---|
| | Initial Fraction | Main Fraction | Post Fraction | Residue | Initial Fraction | Main Fraction | Post Fraction | Residue |
| Methanol | 46.7 | 0.1 | 0 | 0 | 46.7 | 0.1 | 0 | 0 |
| Trimethoxysilane | 51.8 | 99.3 | 0.8 | 0 | 51.6 | 99.2 | 0.9 | 0 |
| Tetramethoxysilane | 0.5 | 0.4 | 97.1 | 2.4 | 0.6 | 0.4 | 96.8 | 2.6 |
| Others | 0.9 | 0.2 | 1.1 | 97.6 | 1.1 | 0.2 | 2.3 | 97.4 |

EXAMPLE 10

To a reaction mixture obtained in a similar manner as in Example 9 was added methyl chloride, to obtain a mixture having the following composition: trimethoxysilane, 50 wt %; tetramethoxysilane, 20 wt %; unreacted methyl alcohol, 25 wt %; methyl chloride, 1.5 wt %; and other compounds, 3.5 wt %.

The resulting mixture was charged into a stainless steel container fitted with a calcium chloride cylinder at its gas outlet. It was allowed to stand in a room maintained at a temperature of 15° to 20° C. The composition of the mixture was analyzed by gas chromatography at an interval of 10 days, in order to examine the changes, with the lapse of time, in the content of trimethoxysilane and tetramethoxysilane. Results obtained are shown in Table 3.

TEST EXAMPLE 1

A sample mixture was prepared by adding 32 g of methyl alcohol and 4.6 g (2.9 wt %) of methyl chloride to 122 g of trimethoxysilane of 99 wt % purity. The changes, with the lapse of time, in the content of trimethoxysilane and tetramethoxysilane were determined as in Example 10. Results obtained are shown in Table 3.

TEST EXAMPLE 2

A sample mixture was prepared in a similar manner as in Test Example 1, except that methyl chloride was not added at all. The changes in the content of trimethoxysilane and tetramethoxysilane were determined with the lapse of time. Results obtained are shown in Table 3.

TEST EXAMPLE 3

A sample mixture was prepared by adding 46 g of ethyl alcohol and 6.3 g (2.9 wt %) of ethyl chloride to 164 g of triethoxysilane of 99 wt % purity. The changes, with the lapse of time, in the content of triethoxysilane and tetraethoxysilane were determined as in Example 10. Results obtained are shown in Table 3.

TEST EXAMPLE 4

A sample mixture was prepared in a similar manner as in Test Example 3, except that ethyl chloride was not added at all. The changes in the content of triethoxysilane and tetraethoxysilane were determined with the lapse of time. Results obtained are shown in Table 3.

TABLE 3

|  |  | Initial | After 10 Days | After 20 Days | After 30 Days |
|---|---|---|---|---|---|
| Example 10 | TMS | 50.0 | 49.1 | 48.7 | 48.1 |
|  | QMS | 20.0 | 20.2 | 21.3 | 22.0 |
| Test Example 1 | TMS | 77.0 | 75.9 | 75.3 | 74.4 |
|  | QMS | 0 | 1.2 | 2.3 | 3.5 |
| Test Example 2 | TMS | 77.0 | 63.3 | 57.0 | 51.3 |
|  | QMS | 0 | 17.3 | 25.2 | 32.3 |
| Test Example 3 | TES | 75.0 | 74.0 | 73.1 | 72.4 |
|  | QES | 0 | 1.4 | 2.6 | 3.5 |
| Test Example 4 | TES | 75.0 | 69.7 | 65.0 | 62.7 |
|  | QES | 0 | 9.6 | 15.7 | 18.6 |

[Notes]
TMS: Trimethoxysilane
QMS: Tetramethoxysilane
TES: Triethoxysilane
QES: Tetraethoxysilane

What is claimed is:

1. A process for producing trialkoxysilanes, comprising:
    (a) contacting silicon with a copper catalyst to create a mixture and activating the mixture;
    (b) reacting an alcohol with the activated silicon and copper mixture to produce a reaction mixture containing trialkoxysilanes;
    (c) purifying the reaction mixture; and
introducing an organic halide into any one of steps a-c above.

2. A process for producing trialkoxysilanes as defined in claim 1, wherein said silicon and said copper catalyst are activated in said activation step by allowing them to contact halide in a liquid or gas phase.

3. A process for producing trialkoxysilanes as defined in claim 2, wherein said activation is carried out in a liquid phase at a temperature of 100° to 500° C.

4. A process for producing trialkoxysilanes as defined in claim 2, wherein said activation is carried out in a gas phase at a temperature of 150° to 650° C.

5. A process for producing trialkoxysilanes as defined in claim 1, wherein said organic halide is a member selected from the group consisting of alkyl halides, alkenyl halides and aryl halides.

6. A process for producing trialkoxysilanes as defined in claim 2, wherein said organic halide is used in an amount of 0.0001 to 1 mol, per mol of said silicon.

7. A process for producing trialkoxysilanes as defined in claim 1, wherein the organic halide is added to the reaction system in said reaction step where said silicon is reacted with said alcohol.

8. A process for producing trialkoxysilanes as defined in claim 7, wherein said organic halide is used in an amount of 0.0001 to 1 mol, per mol of said alcohol.

9. A process for producing trialkoxysilanes as defined in claim 1, wherein said halide is added in said purification step to said reaction mixture containing unreacted alcohol.

10. A process for producing trialkoxysilanes as defined in claim 9, wherein said organic halide is used in an amount of 0.0001 to 20% by weight, based on the amount of said reaction mixture.

11. A process for producing trialkoxysilanes as defined in claim 1, wherein said alcohol is a lower alcohol.

12. A process for producing trialkoxysilanes as defined in claim 1, wherein said reaction of said metallic silicon with said alcohol is carried out at a temperature of 100° to 300° C.

* * * * *

UNITED STATES PATENT AND TRADEMARK OFFICE
CERTIFICATE OF CORRECTION

PATENT NO. : 4,931,578

DATED : June 5, 1990

INVENTOR(S) : OHTA et al

It is certified that error appears in the above-identified patent and that said Letters Patent is hereby corrected as shown below:

On the cover page, after Item [76] insert:

--[73] Assignees: Tama Chemicals Co., Ltd, Tokyo, Japan; Moses Lake Industries, Inc., Moses Lake, WA.--.

Signed and Sealed this

Twenty-ninth Day of October, 1991

*Attest:*

HARRY F. MANBECK, JR.

*Attesting Officer*        *Commissioner of Patents and Trademarks*